(12) United States Patent
Meglan et al.

(10) Patent No.: US 11,647,888 B2
(45) Date of Patent: May 16, 2023

(54) COMPENSATION FOR OBSERVER MOVEMENT IN ROBOTIC SURGICAL SYSTEMS HAVING STEREOSCOPIC DISPLAYS

(71) Applicant: Covidien LP, Mansfield, MA (US)

(72) Inventors: Dwight Meglan, Westwood, MA (US); Albert Dvornik, Somerville, MA (US)

(73) Assignee: Covidien LP, Mansfield, MA (US)

( * ) Notice: Subject to any disclaimer, the term of this patent is extended or adjusted under 35 U.S.C. 154(b) by 92 days.

(21) Appl. No.: 17/048,896

(22) PCT Filed: Apr. 1, 2019

(86) PCT No.: PCT/US2019/025096
§ 371 (c)(1),
(2) Date: Oct. 19, 2020

(87) PCT Pub. No.: WO2019/204012
PCT Pub. Date: Oct. 24, 2019

(65) Prior Publication Data
US 2021/0243427 A1    Aug. 5, 2021

Related U.S. Application Data

(60) Provisional application No. 62/660,398, filed on Apr. 20, 2018.

(51) Int. Cl.
*A61B 34/30* (2016.01)
*H04N 13/344* (2018.01)
(Continued)

(52) U.S. Cl.
CPC ........ *A61B 1/00009* (2013.01); *A61B 1/0005* (2013.01); *A61B 1/00042* (2022.02);
(Continued)

(58) Field of Classification Search
None
See application file for complete search history.

(56) References Cited

U.S. PATENT DOCUMENTS

| | | | |
|---|---|---|---|
| 6,132,368 A | 10/2000 | Cooper | |
| 6,206,903 B1 | 3/2001 | Ramans | |

(Continued)

FOREIGN PATENT DOCUMENTS

| | | |
|---|---|---|
| WO | 0122149 A1 | 3/2001 |
| WO | 2017210101 A1 | 12/2017 |

OTHER PUBLICATIONS

Extended European Search Report dated Dec. 23, 2021 corresponding to counterpart Patent Application EP 19789525.3.
(Continued)

*Primary Examiner* — Samuel D Fereja
(74) *Attorney, Agent, or Firm* — Carter, DeLuca & Farrell LLP

(57) ABSTRACT

Systems and methods for compensating for observer movement during robotic surgery. An exemplary system includes an image capture device configured to capture images of a surgical site, a stereoscopic display device, a sensor configured to detect positions of an observer, and a computing device including a processor and a memory storing instructions. The instructions, when executed by the processor, cause the computing device to receive the images of the surgical site from the image capture device, receive data from the sensor indicating a position of the observer, process the received images of the surgical site based on the movement of the observer, and cause the stereoscopic display device to display the processed images of the surgical site.

24 Claims, 5 Drawing Sheets

(51) Int. Cl.
*A61B 1/005* (2006.01)
*A61B 1/00* (2006.01)
*A61B 90/00* (2016.01)

(52) U.S. Cl.
CPC ...... *A61B 1/00149* (2013.01); *A61B 1/00193* (2013.01); *A61B 34/30* (2016.02); *A61B 90/37* (2016.02); *H04N 13/344* (2018.05)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,549,641 B2 | 4/2003 | Ishikawa et al. |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,757,422 B1 | 6/2004 | Suzuki et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,121,946 B2 | 10/2006 | Paul et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |

(56) References Cited

U.S. PATENT DOCUMENTS

| | | |
|---|---|---|
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,780,178 B2 | 7/2014 | Koh et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,292,734 B2 | 3/2016 | Zhu et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |

(56) References Cited

U.S. PATENT DOCUMENTS

| | | | |
|---|---|---|---|
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 2003/0012425 A1 | 1/2003 | Suzuki et al. | |
| 2007/0176914 A1* | 8/2007 | Bae | H04N 13/398 348/E13.059 |
| 2009/0268015 A1 | 10/2009 | Scott et al. | |
| 2012/0127203 A1 | 5/2012 | Imai | |
| 2012/0127302 A1 | 5/2012 | Imai | |
| 2014/0038635 A1 | 2/2014 | Ngo et al. | |
| 2014/0247329 A1 | 9/2014 | Nakamura et al. | |
| 2015/0035953 A1 | 2/2015 | Bredehoft et al. | |
| 2015/0192996 A1* | 7/2015 | Katou | G06F 3/04886 345/173 |
| 2016/0142683 A1* | 5/2016 | Seesselberg | H04N 7/183 348/143 |
| 2017/0112368 A1* | 4/2017 | Stern | A61B 34/37 |
| 2017/0172675 A1* | 6/2017 | Jarc | A61B 17/00234 |
| 2018/0092706 A1 | 4/2018 | Anderson et al. | |
| 2019/0110843 A1* | 4/2019 | Ummalaneni | A61B 50/13 |
| 2020/0169724 A1* | 5/2020 | Meglan | A61B 34/35 |
| 2021/0361379 A1* | 11/2021 | Ramirez Luna | H04N 13/156 |

OTHER PUBLICATIONS

European Search Report dated Jul. 12, 2019, and Written Opinion Completed Jul. 10, 2019, International Patent Application No. PCT/US2019/025096 9 pages.

Tobii, e-book, tech.tobii.com. Copyright 2021, Tobii AB, "5 Ways Next-Generation Surgical Robotics Will Leverage Attention to Enhance Care", p. 1/12-12/12.

Tobii, Tobii White Paper, tech.tobii.com., May 2020, Version 1.0, "Why Next-Generation Surgical Systems Will Include Eye Tracking", p. 1/15-15/15.

* cited by examiner

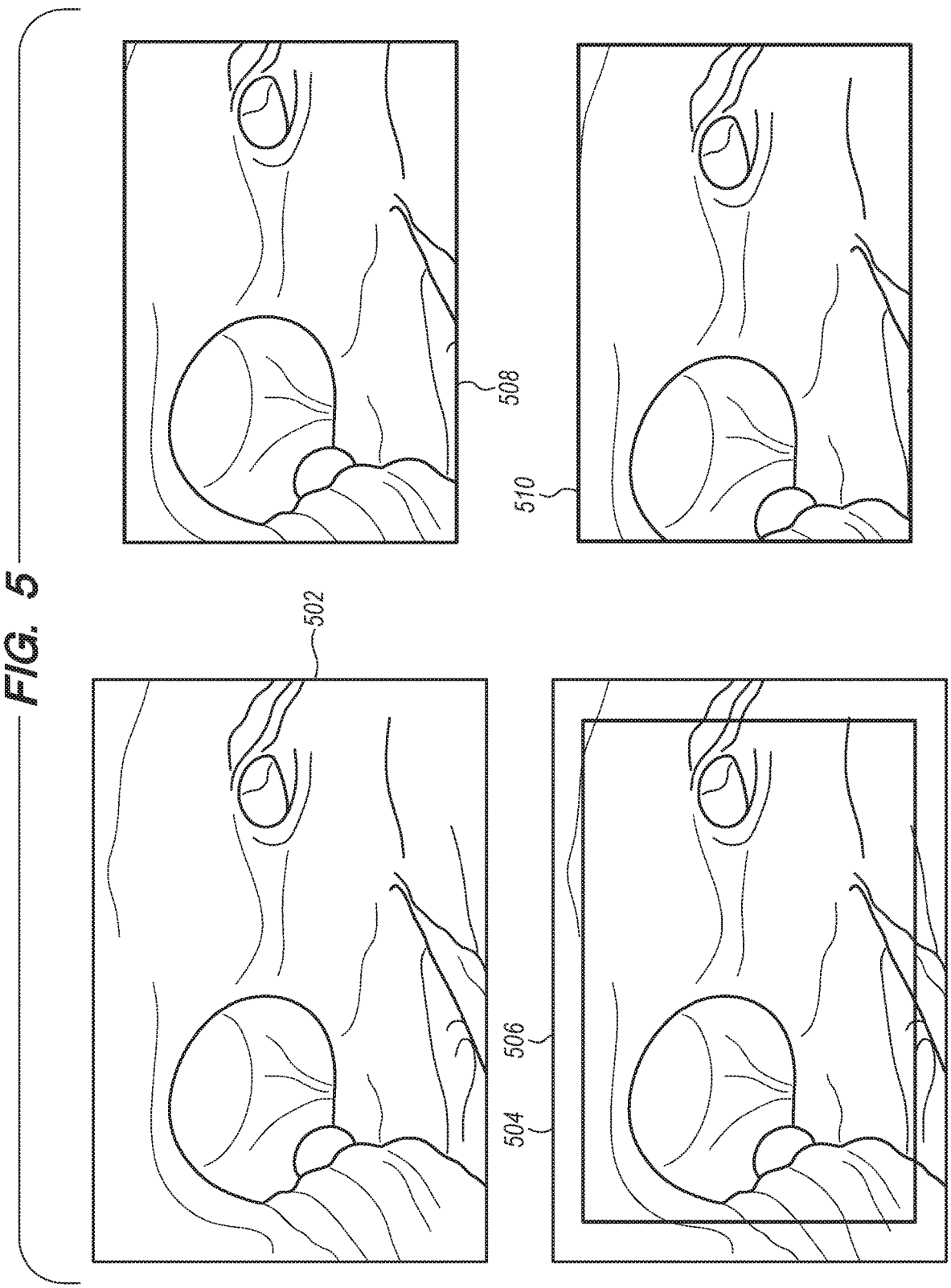

COMPENSATION FOR OBSERVER MOVEMENT IN ROBOTIC SURGICAL SYSTEMS HAVING STEREOSCOPIC DISPLAYS

CROSS-REFERENCE TO RELATED APPLICATIONS

This application is a U.S. National Stage Application filed under 35 U.S.C. § 371(a) of International Patent Application Serial No. PCT/US2019/025096, filed Apr. 1, 2019, which claims the benefit of and priority to U.S. Provisional Patent Application Ser. No. 62/660,398, filed Apr. 20, 2018, the entire disclosure of which is incorporated by reference herein.

BACKGROUND

Description of Related Art

Robotic surgery involves a clinician, such as a surgeon or technician, operating a surgical robot via a control console. Robotic surgery may be performed endoscopically, and thus the only view of a surgical site available to the clinician may be images, such as three-dimensional (3D) or stereoscopic images, captured by an endoscopic camera. While operating the surgical robot, and thus viewing the 3D images, the clinician's head may be moved. Such movement of the clinician's head may cause the clinician to expect corresponding movement of the 3D images, for instance, based on a change in the clinician's perspective. However, conventional 3D video images are not configured to move based on movement of the clinician's head. Thus, if the clinician's head is moved while the clinician views the 3D images, the 3D images that the clinician perceives are somewhat different from the 3D images that the clinician expects to perceive. This difference may be even greater in surgical robotic systems that utilize head or gaze tracking to control movement of the robotic arm coupled to the endoscopic camera. In view of the foregoing, it would be beneficial to have improved systems and methods for controlling and displaying stereoscopic images from an endoscopic camera while controlling a surgical robot during robotic surgery.

SUMMARY

The present disclosure describes robotic surgical systems with observer movement compensation, in accordance with various embodiments. In an aspect of the present disclosure, an illustrative system includes an image capture device configured to capture images of a surgical site, a stereoscopic display device, a sensor configured to detect positions of an observer, and a computing device including at least one processor and a memory storing instructions. When executed by the at least one processor, the instructions cause the computing device to receive the images of the surgical site from the image capture device, receive data from the sensor indicating a first position of the observer, process the received images of the surgical site based on the first position of the observer, and cause the stereoscopic display device to display the processed stereoscopic images of the surgical site.

In embodiments, the images of the surgical site include left-eye image data and right-eye image data.

In some embodiments, the images of the surgical site have a frame size, and the processing the received images of the surgical site based on the first position of the observer includes determining a portion of the images to display based on the first position of the observer, the portion of the images to display being smaller than the frame size.

In another embodiment, the portion of the images to display corresponds to a number of pixels less than the number of pixels included in the images of the surgical site.

In an embodiment, the determining the portion of the images to display includes cropping at least a portion of the images.

In embodiments, the determining the portion of the images to display includes shifting at least a portion of the images.

In some embodiments, the shifting of at least the portion of the images includes determining a vector of movement of the observer based on the first position of the observer, determining a direction and an amount of pixels to shift based on the determined vector of movement of the observer, and shifting at least a portion of the images based on the determined direction and amount of pixels to shift.

In additional embodiments, the determining the vector of movement of the observer further includes determining a degree of movement, and the determining the direction and the amount of pixels to shift is further based on the determined degree of movement.

In another embodiment, the determining the direction and the amount of pixels to shift is further based on a relationship between the vector of movement of the observer and the direction and amount of pixels to shift. The relationship may be based on a table or a threshold.

In embodiments, the determining of the vector of movement of the observer includes determining whether the first position of the observer approaches a maximum threshold, and providing an alert indicating that the first position of the observer approaches the maximum threshold.

In an embodiment, the determining the vector of movement of the observer includes determining whether the first position of the observer exceeds a maximum threshold, and providing an alert indicating that the first position of the observer exceeds the maximum threshold.

In another embodiment, the system further includes a surgical robot, wherein the image capture device is coupled to the surgical robot, and the instructions, when executed by the processor, further cause the computing device to determine a vector of movement of the observer based on the data received from the sensor; and cause the surgical robot to reposition the image capture device based on the determined vector of movement of the observer.

In some embodiments, the stereoscopic display is an autostereoscopic display.

In several embodiments, the stereoscopic display is a passive stereoscopic display, and the system further comprises three-dimensional (3D) glasses worn by the observer.

In embodiments, the 3D glasses cause a left-eye image to be displayed to a left eye of the observer, and a right-eye image to be displayed to a right eye of the observer.

In an embodiment, the image capture device is a stereoscopic camera coupled to an endoscope.

In another embodiment, the sensor is a motion sensor or a camera.

In some embodiments, the data received from the sensor indicating a first position of the observer includes an image of the observer, and the instructions, when executed by the processor, further cause the computing device to generate second image data based on the image of the observer, and detect the first position of the observer by processing the second image data.

In several embodiments, the detecting first position of the observer includes detecting one or more of a distance of the observer relative to a vector normal to the stereoscopic display, a direction of the observer relative to the vector normal to the stereoscopic display, or an orientation of the observer relative to the stereoscopic display.

In embodiments, the direction of the observer is one or more of a lateral direction or a vertical direction.

In some embodiments, the instructions, when executed by the at least one processor, further cause the computing device to receive additional data from the sensor indicating a second position of the observer, process the received images of the surgical site based on the second position of the observer, and cause the stereoscopic display to display the processed images of the surgical site.

Provided in accordance with embodiments of the present disclosure are methods for compensating for observer movement in a robotic surgical system. In an aspect of the present disclosure, an illustrative method includes receiving images of a surgical site from an image capture device, receiving data from a sensor indicating a first position of an observer, processing the received images of the surgical site based on the first position of the observer, and causing a stereoscopic display device to display the processed images of the surgical site.

Provided in accordance with embodiments of the present disclosure are non-transitory computer-readable storage media storing a program for compensating for observer movement in a robotic surgical system. In an aspect of the present disclosure, an illustrative program includes instructions which, when executed by a processor, cause a computing device to receive images of a surgical site from an image capture device, receive data from a sensor indicating a first position of an observer, process the received images of the surgical site based on the first position of the observer, and cause a stereoscopic display device to display the processed images of the surgical site.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein:

FIG. 5 shows various views of an exemplary graphical user interface that may be displayed by the computing device of FIG. 2, according to an embodiment of the present disclosure.

DETAILED DESCRIPTION

The present disclosure generally relates to the display of stereoscopic images on a three-dimensional (3D) display and, more particularly, to the mitigation of a head-movement effect that is perceived by a user when viewing stereoscopic images on a conventional 3D display. In that regard, the present disclosure relates to systems and methods for compensating for observer movement in robotic surgical systems having stereoscopic displays, such as by detecting movement of the observer, repositioning an endoscopic camera based on the detected movement of the observer, shifting images received from the endoscopic camera based on the detected movement of the observer to compensate for the movement of the observer, and displaying the shifted images on a stereoscopic display. In this manner, the stereoscopic images are cropped and/or shifted, such as by shifting one or more lines and/or columns of pixels around the edges of the stereoscopic images, based on movement of the observer's head prior to being displayed. The effect of such shifting of the stereoscopic images is that the observer's perceived movement of the stereoscopic images caused by movement of the observer's head is visually mitigated by changing a displayed portion of the stereoscopic images to cause the displayed images to "move" in the way the observer expects the stereoscopic images to move even if the images received from the endoscopic camera do not move. Visual and/or auditory guidance, notifications, and/or alarms may be displayed and/or emitted by the stereoscopic display and/or a computing device associated therewith, to assist the observer with appropriately moving the observer's body, head, face, and/or eyes to control movement of the endoscopic camera and/or shifting of the images. Those skilled in the art will appreciate that the endoscopic camera may also be controlled based on other user interfaces, and thus need not be controlled based on movement of the observer.

Figure 1:
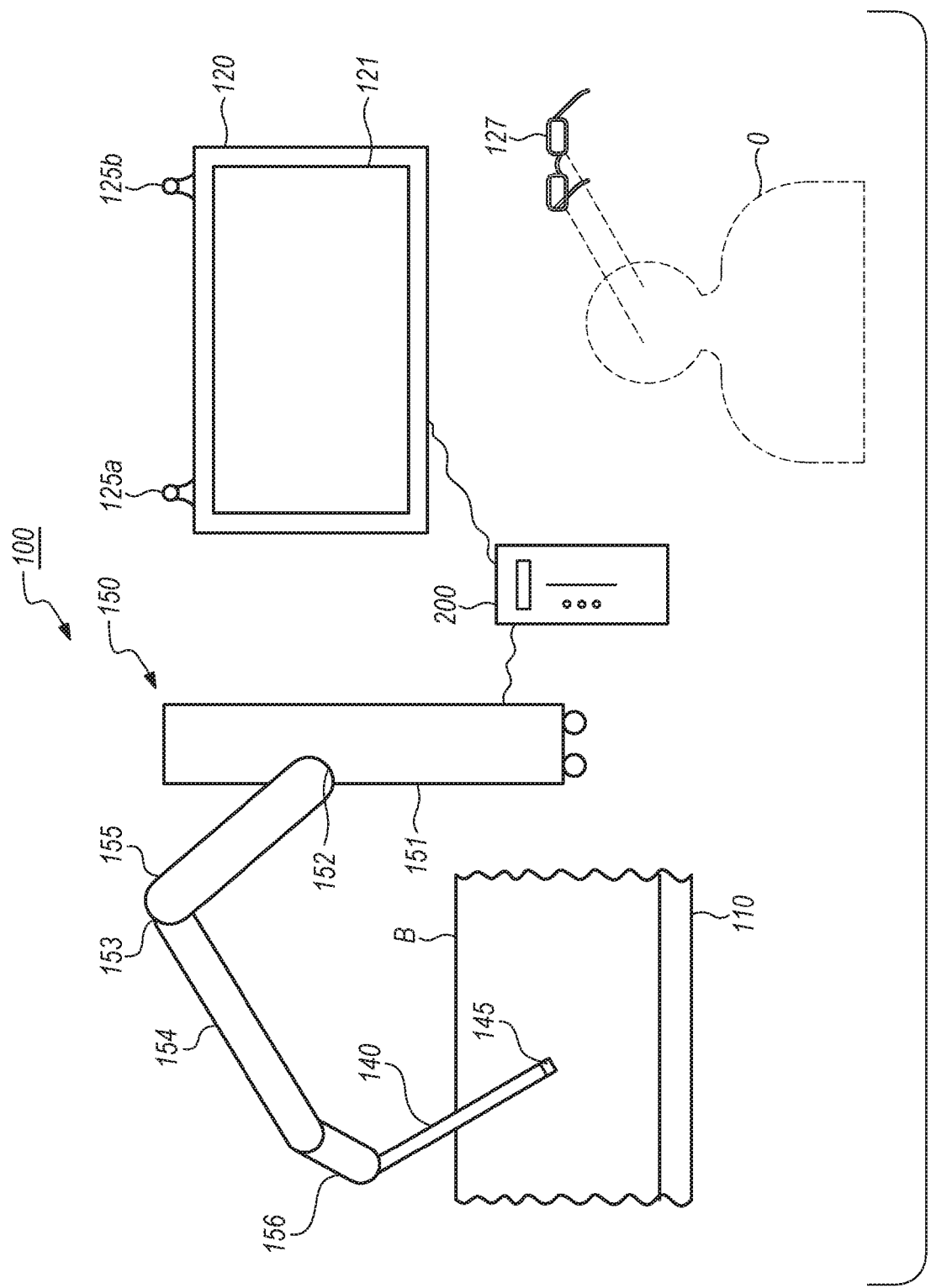
FIG. 1 is a schematic diagram of an exemplary robotic surgical system that may be used to compensate for observer movement, according to an embodiment of the present disclosure.

With reference to FIG. 1, there is shown a system 100 for compensating for observer movement in robotic surgical systems having stereoscopic displays, according to an embodiment of the present disclosure. System 100 includes a table 110 supporting a body B, a stereoscopic display device 120, one or more image capture devices 125a and 125b, an endoscope 140 including an endoscopic camera 145, a surgical robot assembly 150, and a computing device 200. FIG. 1 further shows the observer O. The observer may be a user, clinician, surgeon, nurse, technician, and/or any other person operating surgical robot assembly 150.

Endoscopic camera 145 may be a single camera or a plurality of cameras capable of capturing stereoscopic images and/or any other camera or imaging device known to those skilled in the art that may be used to capture 3D images of a surgical site. In some embodiments, endoscopic camera 145 is a dual-lens or multi-lens camera. Display 120 may be any stereoscopic display device configured to output stereoscopic images to the observer. For example, display 120 may be an autostereoscopic display, a passive stereoscopic display, and/or any other display device configured to display three-dimensional (3D) images known to those skilled in the art. In embodiments where display 120 is a passive stereoscopic display device, system 100 may further include 3D glasses 127 worn by the observer. For example, 3D glasses 127 may cause a left-eye image to be displayed to a left eye of the observer, and a right-eye image to be displayed to a right eye of the observer.

Image capture devices 125a and 125b, may be any image capture devices known to those skilled in the art, such as video cameras, still cameras, stereoscopic cameras, etc. In some embodiments, image capture devices 125a and 125b are motion sensors configured to detect movement of the observer. In other embodiments, image capture devices 125a, 125b are infrared light based marker tracking devices configured to track markers attached to the observer, such as to the observer's head and/or to 3D glasses 127. In embodiments, image capture devices 125a and 125b are positioned about display 120 to detect a viewing direction and/or angle of the observer. Image capture devices 125a and 125b, are referred to collectively hereinafter as image capture devices 125.

Surgical robot assembly 150 includes a base 151, a first joint 152 coupled to base 151, a first robotic arm 155, coupled to first joint 152, a second joint 153 coupled to first robotic arm 155, a second robotic arm 154 coupled to second joint 153, and an instrument drive unit 156 coupled to second arm 154. Endoscope 140 is attached to surgical robot assembly 150 via instrument drive unit 156. In embodiments, multiple surgical robot assemblies 150 may be used concurrently and may together form a surgical robot. While a single surgical robot assembly 150 is shown in FIG. 1, multiple surgical robot assemblies 150 may be included in the surgical training environment, and those skilled in the art will recognize that the below-described methods may be applied using surgical robots having single and/or multiple surgical robot assemblies 150, each including at least one base 151, robotic arms 154 and 155, joints 152 and 153, and instrument drive unit 156, without departing from the scope of the present disclosure. Body B may be a body of a patient upon whom a robotic surgical procedure is being performed.

Computing device 200 may be any computing device configurable for use during robotic surgery known to those skilled in the art. For example, computing device 200 may be a desktop computer, laptop computer, server and terminal configuration, and/or a control computer for surgical robot assembly 150, etc. In some embodiments, computing device 200 may be included in display 120. As described further below, system 100 may be used during robotic surgery to detect movement of the observer, reposition endoscope 140 based on the detected movement, and shift images captured by endoscopic camera 145 based on the detected movement.

Figure 2:
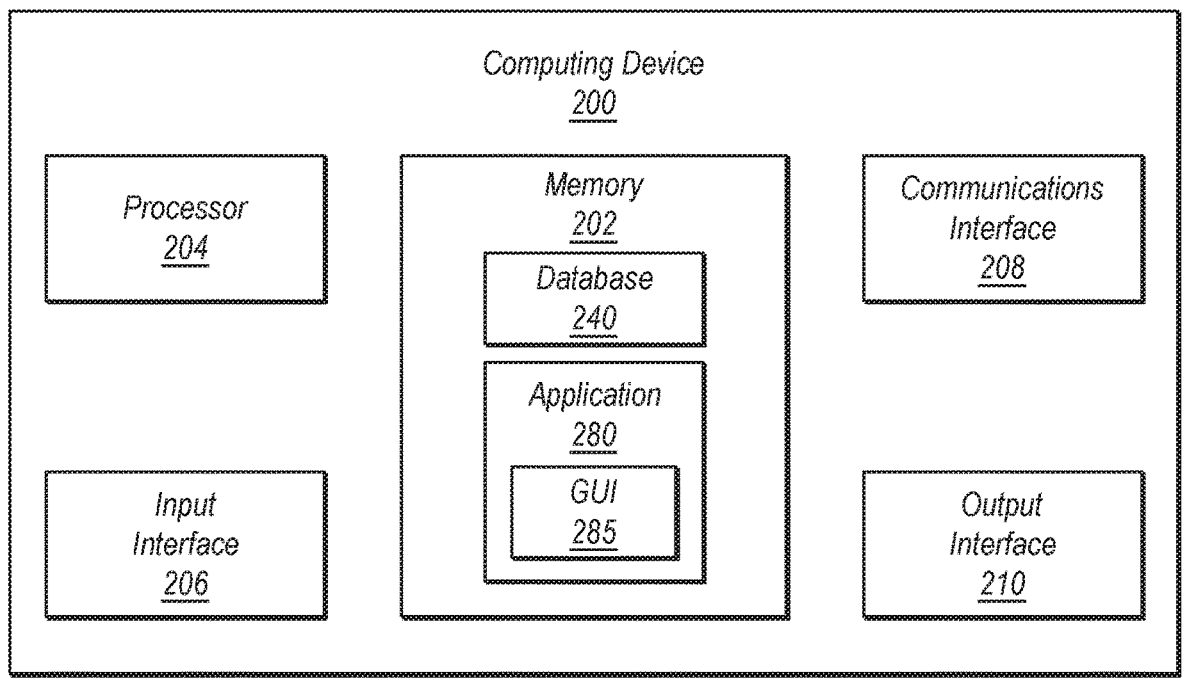
FIG. 2 is a simplified block diagram of an exemplary computing device forming part of the system of FIG. 1.

Turning now to FIG. 2, there is shown a schematic diagram of computing device 200 forming part of system 100 of FIG. 1, according to an embodiment of the present disclosure. Computing device 200 includes a memory 202 storing a database 240 and an application 280. Application 280 includes instructions which, when executed by a processor 204, cause computing device 200 to perform various functions, as described below. Application 280 further includes graphical user interface (GUI) instructions 285 which, when executed by processor 204, cause computing device 200 to generate one or more GUIs (not shown in FIG. 2), such as, for example, the exemplary GUI shown in FIGS. 5A-5D. Database 240 stores various tables, thresholds, and/or relational data related to shifting of images based on movement of the observer, as further described below.

Memory 202 may include any non-transitory computer-readable storage medium for storing data and/or software that is executable by processor 204 and which controls the operation of computing device 200, display 120, and/or surgical robot assembly 150. In an embodiment, memory 202 may include one or more solid-state storage devices such as flash memory chips. Alternatively, or in addition to the one or more solid-state storage devices, memory 202 may include one or more mass storage devices connected to the processor 204 through a mass storage controller (not shown in FIG. 2) and a communications bus (not shown in FIG. 2). Although the description of computer-readable media included herein refers to a solid-state storage, it should be appreciated by those skilled in the art that computer-readable storage media may be any available media that can be accessed by processor 204. That is, computer-readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which may be used to store the desired information and which may be accessed by computing device 200.

Computing device 200 further includes an input interface 206, a communications interface 208, and an output interface 210. Input interface 206 may be a mouse, keyboard, or other hand-held controller, foot pedal, touch screen, voice interface, and/or any other device or interface by means of which a user may interact with computing device 200.

Communications interface 208 may be configured to connect to a network such as a local area network (LAN) consisting of a wired network and/or a wireless network, a wide area network (WAN), a wireless mobile network, a Bluetooth network, and/or the internet. Output interface 210 may be a screen or other display device usable to output images or data by computing device 200.

Figure 3:
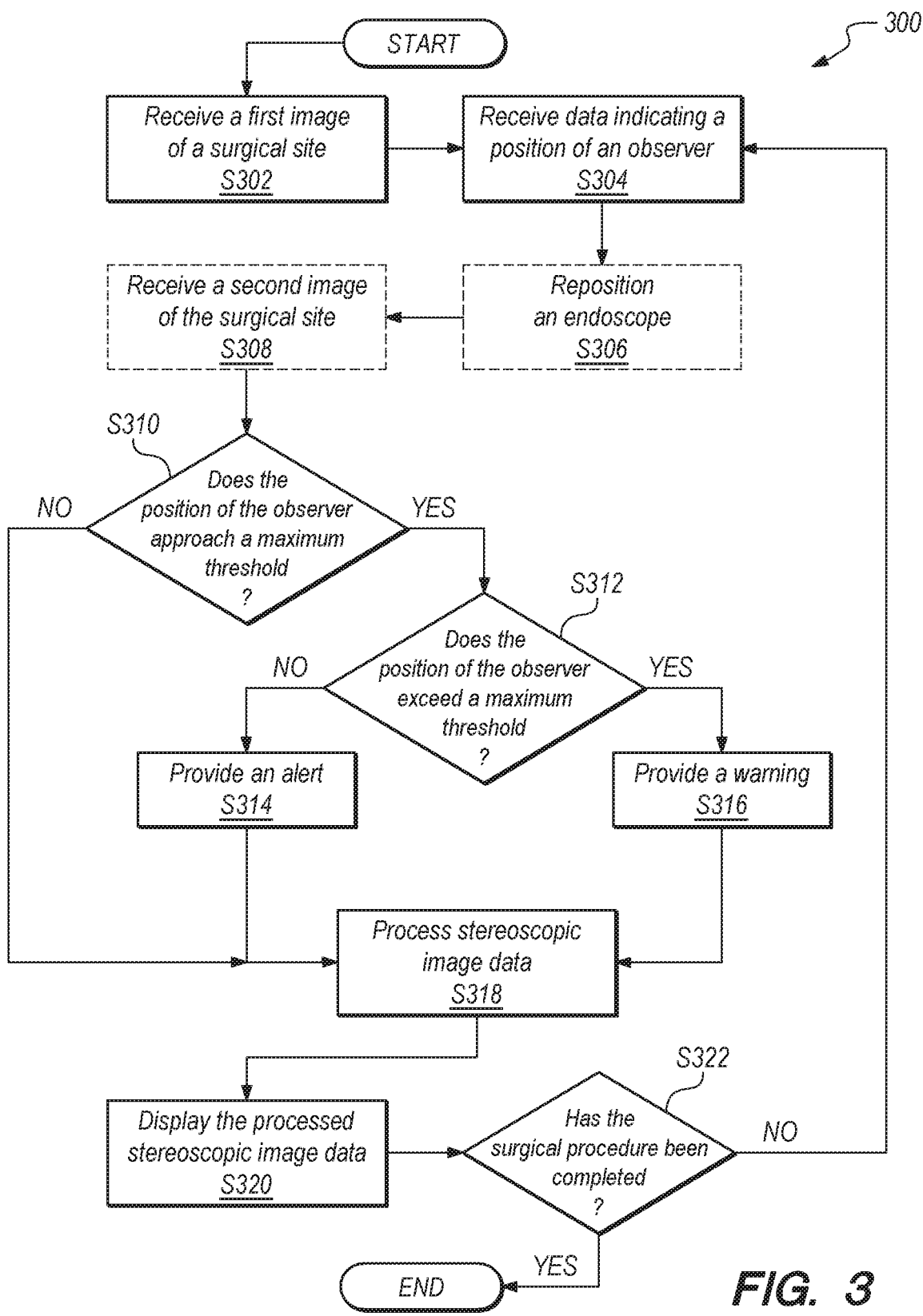
FIG. 3 is a flowchart of an exemplary method for compensating for observer movement in a robotic surgical system having a stereoscopic display, according to an embodiment of the present disclosure.

With reference to FIG. 3, there is shown a flowchart of an exemplary method 300 for compensating for observer movement in robotic surgical systems having stereoscopic displays, according to an embodiment of the present disclosure. In embodiments, method 300 may be implemented using a system, such as system 100 of FIG. 1, and one or more computing devices, such as computing device 200 of FIG. 2. Starting at step S302, computing device 200 receives one or more images of a surgical site within body B. The images may be first images of the surgical site, and may be captured by endoscopic camera 145. The first images may be stereoscopic images including left-eye image data and right-eye image data. In some embodiments, the first images are live images of the surgical site, and the below-described processing of the first images occurs in real time.

Next, at step S304, computing device 200 receives data indicating a position of the observer. The data may be acquired by image capture devices 125. The data may include images and/or image data of the observer, such as images of a portion of the observer's body, for example, the observer's head, face, and/or eyes. For example, if the data received from image capture devices 125 include images, computing device 200 may process the images to generate image data, and may then further process the image data to identify the observer and detect a position of the observer in the image data, such as a position relative to a vector normal and centered to a front face of display 120 (referred to hereinafter as the "normal vector"). For example, the normal vector may be a vector coming out of the center of a face of display 120 facing the observer. In some embodiments, computing device 200 may process the images and/or image data received from image capture devices 125 to identify the observer's head, face, and/or eyes, as well as a viewing direction, orientation, and/or angle of the observer's head, face, and/or eyes. Computing device 200 may further process the images and/or image data received from image capture devices 125 to determine movement of the observer's body, head, face, and/or eyes, such as movement relative to the normal vector. For example, computing device 200 may intermittently and/or continuously receive data from image capture devices 125, and may intermittently and/or continuously process the data to identify successive positions of the observer, and thereby determine movement of the observer relative to a previous position and/or relative to the normal vector. In other embodiments, such as embodiments where image capture devices 125 are motion sensors, image capture devices 125 provide motion data to computing device 200.

As an optional step, at step S306, computing device 200, such as via application 280, may process the data received at step S304 to determine a direction, amount, speed, and/or degree of movement of the observer based on the determined position or positions of the observer, such as of the observer's head, face, and/or eyes. For example, computing device 200 may determine whether the observer is moving in a horizontal direction, a vertical direction, a diagonal direction, and/or a rotational direction relative to the normal vector. Computing device 200 may further determine an amount, speed, and/or degree of movement of the observer in each direction—e.g., the user may be moving left by 5 cm and up by 2 cm. Computing device 200 may then cause surgical robot assembly 150 to reposition endoscope 140 based on the determined movement of the observer.

As noted above, in some embodiments, computing device 200 may intermittently and/or continuously receive images and/or image data of the observer from image capture devices 125. Computing device 200 may then intermittently and/or continuously process the images and/or image data of the observer to detect movement of the observer. For example, computing device 200 may determine successive positions of the observer relative to the normal vector in the images and/or image data received from image capture devices 125. Computing device 200 may then determine a vector of the observer's movement based on the determined successive positions of the observer relative to the normal vector in the images and/or image data.

As an additional optional step, after endoscope 140 is repositioned, computing device 200, at step S308, receives second images of the surgical site from endoscopic camera 145. Similar to the first images, the second images may be stereoscopic images including left-eye image data and right-eye image data, and may have the same aspect ratio, resolution, frame size, and/or number of pixels as the first images.

Thereafter, concurrently with steps S306 and/or S308, or in embodiments where steps S306 and S308 are not performed directly after step S304, at step S310 computing device 200, such as via application 280, determines whether the position of the observer, as determined at step S306, approaches a maximum threshold for that particular direction of movement. For example, computing device 200 may have stored in database 240 various tables and/or thresholds for each direction relative to the normal vector. The tables and/or thresholds may indicate various relationships between the direction and distance of the observer relative to the normal vector, and corresponding movement of endoscope 140 and/or adjustment required for displaying stereoscopic image data. For example, the tables and/or thresholds may indicate an amount of movement of the observer in a particular direction, such as a horizontal direction, required to cause surgical robot assembly 150 to reposition endoscope 140 by a predetermined amount in the same direction, and/or a number of pixels in a particular direction to shift stereoscopic images received from endoscope 140 based on position of the observer relative to the normal vector. The tables and/or thresholds may also indicate a maximum amount of movement in a particular direction that can be used to cause surgical robot assembly 150 to reposition endoscope 140 and/or a maximum number of pixels that could be shifted in a particular direction. Such a maximum threshold may correspond to a limit of motion of endoscope 140 and/or surgical robot assembly 150, and/or a maximum number of pixels available to be shifted in a particular direction.

If it is determined at S310 that the position of the observer does not approach a maximum threshold corresponding to that particular direction ("No" at step S310), processing skips ahead to step S318. Alternatively, if it is determined at step S310 that the position of the observer approaches a maximum threshold corresponding to that particular direction ("Yes" at step S310), processing proceeds to step S312. At step S312, computing device 200, such as via application 280, determines whether the position of the observer exceeds the maximum threshold corresponding to that particular direction. If it is determined at step S312 that the position of the observer does not exceed the maximum threshold corresponding to that particular direction ("No" at step S312), processing proceeds to step S314, where computing device 200 provides an alert to notify the observer that the position of the observer is approaching the maximum threshold corresponding to that particular direction. Alternatively, if it is determined at step S312 that the position of the observer exceeds the maximum threshold corresponding to that particular direction ("Yes" at step S312), processing proceeds to step S316, where computing device provides a warning to notify the observer that the position of the observer has exceeded the maximum threshold. After either the alert is provided at step S314 or the warning is provided at step S316, processing proceeds to step S318.

At step S318, computing device 200, such as via application 280, processes the images of the surgical site received at step S302 and/or the second images of the surgical site received at step S308. Further details regarding an exemplary procedure 400 that may be employed as part of the processing of the images of the surgical site at step S318 are described below with reference to FIG. 4. Computing device 200 then, at step S320, causes display 120 to display the processed images of the surgical site.

Thereafter, at step S322, computing device 200, such as via application 280, determines whether the surgical procedure has been completed. For example, computing device 200 may receive input from the observer and/or another clinician involved in the surgical procedure indicating that the surgical procedure has been completed. If it is determined at step S322 that the surgical procedure has not been completed ("No" at step S322), processing returns to step S304. Alternatively, if it is determined at step S322 that the surgical procedure has been completed ("Yes" at step S322), processing ends.

Figure 4:
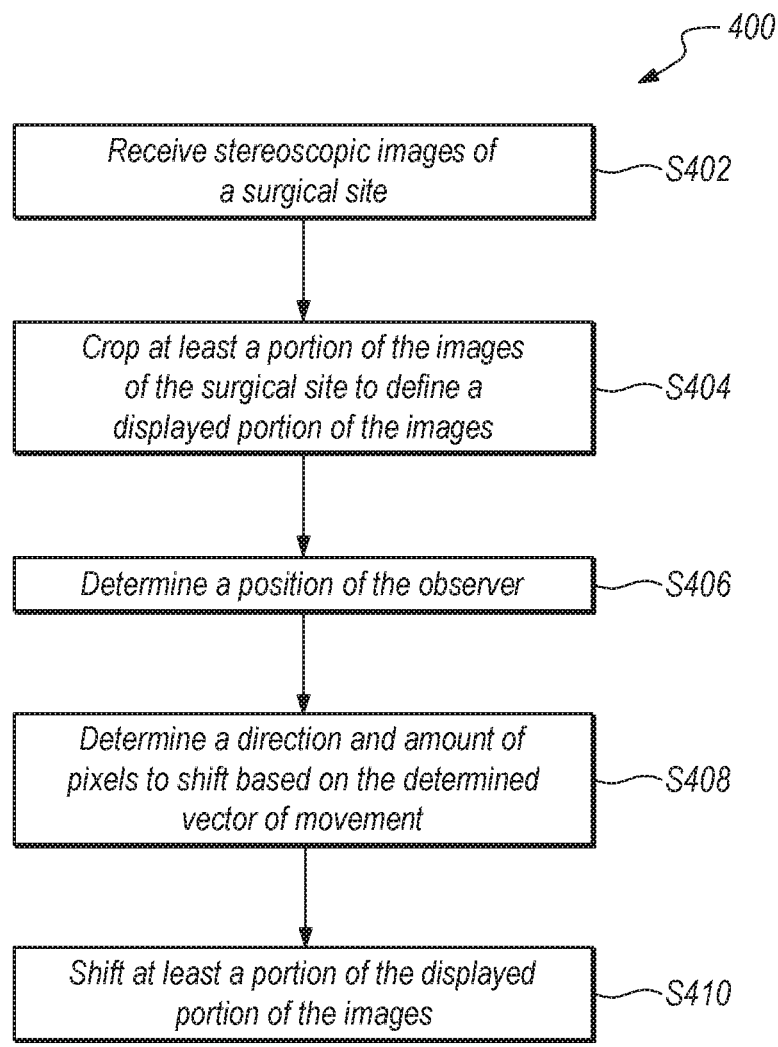
FIG. 4 is a flowchart of an exemplary method for processing stereoscopic image data that compensates for observer movement, according to an embodiment of the present disclosure.

Turning now to FIG. 4, there is shown a flowchart of an exemplary method 400 for processing stereoscopic images to compensate for observer movement, according to an embodiment of the present disclosure. Computing device 200 may perform some or all of the steps of the method of FIG. 4, for example, at or during step S318 of the method 300 of FIG. 3, described above. However, those skilled in the art will recognize that some of the steps of method 400 may be repeated, omitted, and/or performed in a different sequence without departing from the scope of the present disclosure.

Starting at step S402, computing device 200, receives images of a surgical site. The images of the surgical site may be received from a camera such as endoscopic camera 145, as shown in FIG. 5 where, for example, image 502 is a stereoscopic image displayed by display 120. Thus, the images received from endoscopic camera 145 may include left-eye image data and right-eye image data which are displayed by display device 120 as a stereoscopic image 502. The image 502 may have a particular aspect ratio, resolution, frame size, and/or number of pixels. For example, the image 502 may have multiple rows and columns of pixels. The aspect ratio, resolution, frame size, and/or number of pixels may correspond to a type of endoscopic camera 145 used. Alternatively, or in addition, the aspect ratio, resolution, frame size, and/or number of pixels may correspond to image processing techniques used by computing device 200. For example, the frame size of the image 502 may correspond to a number of pixels included in the image 502.

Thereafter, at step S404, computing device 200, such as via application 280, crops at least a portion of the image 502 of the surgical site to designate a displayed portion 504 of the image 502, as shown in FIG. 5. For example, the displayed portion 504 may include a number of pixels less than the full number of pixels included in the image 502 of the surgical site. Thus, the displayed portion 504 may have a smaller resolution, frame size, and/or number of pixels than the image 502 of the surgical site. For example, the displayed portion 504 may exclude one or more rows and/or columns of pixels 506 around outer edges of the image 502 of the surgical site. As shown in FIG. 5, the displayed portion 504 has a smaller frame size than the image 502. Image view 508 shows an example of the displayed portion 504 of the image 502 that may be displayed on display 120 prior to being shifted.

Next, at step S406, computing device 200, such as via application 280, determines a position of the observer's body, e.g. the observer's head, face, and/or eyes, relative to the normal vector. In some embodiments, the determination described above with reference to step S306 is the same as the determination described here. In other embodiments, computing device 200 may perform two separate determinations of a position of the observer relative to the normal vector. For example, computing device 200 may determine a horizontal distance, a vertical distance, and/or a diagonal distance, of the position of the observer relative to the normal vector. In some embodiments, computing device 200 may determine a directional component, such as a vector, and a scalar component, such as a magnitude, based on the position of the observer relative to the normal vector. In some embodiments, successive positions of the observer (such as a first position, a second position, etc.) are determined, and movement of the observer may then be detected based on the determined successive positions of the observer relative to the normal vector. For example, as the observer moves relative to the normal vector, one or more positions of the observer relative to the normal vector may be determined, and a direction, amount, speed, and/or degree of movement of the observer may be determined based on the successive positions of the observer relative to the normal vector.

Thereafter, at step S408, computing device 200, such as via application 280, determines a direction and/or amount of pixels to shift and/or pan the displayed portion 504 of the image 502, based on the position of the observer determined at step S406. The determination may be based on a table and/or a threshold. For example, computing device 200 may have stored in database 240 various tables and/or thresholds, as described above with reference to step S310. The tables and/or thresholds may indicate various relationships between a direction and/or distance of the observer relative to the normal vector, and a corresponding direction and amount of pixels to shift and/or pan the displayed portion 504 of the image 502. For example, the tables and/or thresholds may indicate distance of the observer from the normal vector in a particular direction, such as a horizontal direction, required to shift a predetermined amount of pixels of the image frame 504 in the same direction. In embodiments, different thresholds and/or relationships may be configured for each direction. For example, based on the preference of the observer, the threshold for the horizontal direction may be lower than the threshold for the vertical direction, thus allowing for more sensitivity to movement of the observer in a horizontal direction relative to the normal vector than movement of the observer in a vertical direction relative to the normal vector. The tables and/or thresholds may also indicate a maximum distance of the observer from the normal vector in a particular direction that can be used to shift pixels in that direction. For example, if too many pixels are shifted and/or panned at once, the images displayed by display 120 may appear distorted. As such, a maximum threshold may correspond to a limit of the number of pixels that may be shifted and/or panned at once. Further, in embodiments where computing device 200 determines directional and scalar components based on movement of the observer, the determination of the direction and/or amount of pixels to shift may further be based on the directional and scalar components.

Next, at step S410, computing device 200, such as via application 280, shifts the displayed portion 504 of the image 502 based on the direction and/or amount of pixels to shift determined at step S408. For example, if the position of the observer is to the left of the normal vector by a particular amount, computing device 200 may shift the displayed portion 504 right by the amount of pixels determined at step S408. In the example shown in FIG. 5, the displayed portion 504 of the image 502, as shown in unshifted image view 508, is shifted to the right (as viewed by the observer), as shown in shifted image view 510, such that the displayed portion 504 includes one or more columns of pixels to the right of, and not included in, the unshifted image view 508, and excludes one or more columns of pixels of the image 502 of the surgical site included in the right side of the unshifted image view 508. As such, the unshifted image view 508 and the shifted image view 510, both being based on the image 502 of the surgical site received from endoscopic camera 145, may include an overlapping portion that is the majority of both the unshifted image view 508 and the shifted image view 510. However, the shifted image view 510 includes a minor portion of the right of the shifted image view 510 that is not included in the unshifted image view 508, and will exclude a minor portion of the right of the unshifted image view 508.

As such, by virtue of the above-described systems and methods, computing device 200 may be configured to detect one or more positions of the observer, reposition an endoscopic camera based on movement of the observer determined based on successive positions of the observer, shift one or more lines and/or columns of pixels in the images received from the endoscopic camera based on the one or more positions of the observer to compensate for the movement of the observer, and display the shifted images on a stereoscopic display. In this manner, the stereoscopic images are cropped and/or shifted based on movement of the observer's head prior to being displayed. One effect of such shifting of the stereoscopic images is that the displayed images "move" in the way the observer expects the stereoscopic images to move even if the images received from the endoscopic camera do not move.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

What is claimed is:

1. A robotic surgical system with observer movement compensation, the system comprising:
    a camera configured to capture images of a surgical site;
    a stereoscopic display device;
    a sensor configured to detect positions of an observer; and
    a computing device including at least one processor and a memory storing instructions which, when executed by the at least one processor, cause the computing device to:
        receive the images of the surgical site from the camera,
        receive data from the sensor indicating a first position of the observer,
        process the received images of the surgical site based on the first position of the observer,
        cause the stereoscopic display device to display the processed images of the surgical site,
        determine a vector of movement of the observer based on the first position of the observer,
        determine whether the vector of movement exceeds a threshold corresponding to a maximum amount of movement for which the camera may be repositioned,
        reposition the camera to a new position corresponding to the vector of movement when it is determined that the vector of movement does not exceed the threshold corresponding to the maximum amount of movement for which the camera may be repositioned,
        determine whether the vector of movement exceeds a threshold corresponding to a maximum number of pixels available to be shifted, and
        shift the stereoscopic images when it is determined that:
            the vector of movement does not exceed the threshold corresponding to the maximum number of pixels available to be shifted; and
            the vector of movement exceeds the threshold corresponding to the maximum amount of movement for which the camera may be repositioned.

2. The system according to claim 1, wherein the images of the surgical site include left-eye image data and right-eye image data.

3. The system according to claim 1, wherein the images of the surgical site have a frame size, and
    wherein the processing the received images of the surgical site based on the first position of the observer includes determining a portion of the images to display based on the first position of the observer, the portion of the images to display being smaller than the frame size.

4. The system according to claim 3, wherein the portion of the images to display corresponds to a number of pixels less than the number of pixels included in the images of the surgical site.

5. The system according to claim 3, wherein the determining the portion of the images to display includes cropping at least a portion of the images.

6. The system according to claim 3, wherein the determining the portion of the images to display includes shifting at least a portion of the images.

7. The system according to claim 6, wherein the shifting at least the portion of the images includes:
    determining a direction and an amount of pixels to shift based on the determined vector of movement of the observer; and
    shifting at least a portion of the images based on the determined direction and amount of pixels to shift.

8. The system according to claim 7, wherein the determining the vector of movement of the observer further includes determining a degree of movement, and
    wherein the determining the direction and the amount of pixels to shift is further based on the determined degree of movement.

9. The system according to claim 7, wherein the determining the direction and the amount of pixels to shift is further based on a relationship between the vector of movement of the observer and the direction and amount of pixels to shift.

10. The system according to claim 9, wherein the relationship is based on a table.

11. The system according to claim 1, wherein the computing device is further configured to:
    determine whether the first position of the observer approaches a maximum threshold; and
    provide an alert indicating that the first position of the observer approaches the maximum threshold.

12. The system according to claim 1, wherein the computing device is further configured to:
    determine whether the first position of the observer exceeds a maximum threshold; and
    provide an alert indicating that the first position of the observer exceeds the maximum threshold.

13. The system according to claim 1, wherein the stereoscopic display is an autostereoscopic display.

14. The system according to claim 1, wherein the stereoscopic display is a passive stereoscopic display, and the system further comprises three-dimensional (3D) glasses worn by the observer.

15. The system according to claim 14, wherein the 3D glasses cause a left-eye image to be displayed to a left eye of the observer, and a right-eye image to be displayed to a right eye of the observer.

16. The system according to claim 1, wherein the camera is a stereoscopic camera coupled to an endoscope.

17. The system according to claim 1, wherein the sensor is a motion sensor.

18. The system according to claim 1, wherein the sensor is a second camera.

19. The system according to claim 18, wherein the data received from the sensor indicating a first position of the observer includes an image of the observer, and
    wherein the instructions, when executed by the at least one processor, further cause the computing device to:
        generate second image data based on the image of the observer; and
        detect the first position of the observer by processing the second image data.

20. The system according to claim 19, wherein the detecting the first position of the observer includes detecting one or more of:
    a distance of the observer relative to a vector normal to the stereoscopic display;
    a direction of the observer relative to the vector normal to the stereoscopic display; or an orientation of the observer relative to the stereoscopic display.

21. The system according to claim 20, wherein the direction of the observer is one or more of a lateral direction or a vertical direction.

22. The system according to claim 1, wherein the instructions, when executed by the at least one processor, further cause the computing device to:
receive additional data from the sensor indicating a second position of the observer;
process the received images of the surgical site based on the second position of the observer, and
cause the stereoscopic display device to display the processed images of the surgical site.

23. A method for compensating for observer movement in a robotic surgical system, the method comprising:
receiving images of a surgical site from a camera;
receiving data from a sensor indicating a first position of an observer;
processing the received images of the surgical site based on the first position of the observer;
causing a stereoscopic display device to display the processed images of the surgical site;
determining a vector of movement of the observer based on the first position of the observer,
determining whether the vector of movement exceeds a threshold corresponding to a maximum amount of movement for which the camera may be repositioned,
repositioning the camera to a new position corresponding to the vector of movement when it is determined that the vector of movement does not exceed the threshold corresponding to the maximum amount of movement for which the camera may be repositioned,
determining whether the vector of movement exceeds a threshold corresponding to a maximum number of pixels available to be shifted, and
shifting the stereoscopic images when it is determined that:
the vector of movement does not exceed the threshold corresponding to the maximum number of pixels available to be shifted; and
the vector of movement exceeds the threshold corresponding to the maximum amount of movement for which the camera may be repositioned.

24. A non-transitory computer-readable storage medium storing a program for compensating for observer movement in a robotic surgical system, the program including instructions which, when executed by a processor, cause a computing device to:
receive images of a surgical site from a camera;
receive data from a sensor indicating a first position of an observer;
process the received images of the surgical site based on the first position of the observer;
cause a stereoscopic display device to display the processed images of the surgical site;
determine a vector of movement of the observer based on the first position of the observer,
determine whether the vector of movement exceeds a threshold corresponding to a maximum amount of movement for which the camera may be repositioned,
reposition the camera to a new position corresponding to the vector of movement when it is determined that the vector of movement does not exceed the threshold corresponding to the maximum amount of movement for which the camera may be repositioned,
determine whether the vector of movement exceeds a threshold corresponding to a maximum number of pixels available to be shifted, and
shift the stereoscopic images when it is determined that:
the vector of movement does not exceed the threshold corresponding to the maximum number of pixels available to be shifted; and
the vector of movement exceeds the threshold corresponding to the maximum amount of movement for which the camera may be repositioned.

* * * * *